(12) United States Patent
Frock et al.

(10) Patent No.: US 11,571,221 B2
(45) Date of Patent: Feb. 7, 2023

(54) COMBINED BONE TAP AND RASP

(71) Applicant: Spinal Simplicity, LLC, Overland Park, KS (US)

(72) Inventors: Melissa Frock, Larwill, IN (US); Adam Frock, Larwill, IN (US); Todd Moseley, Olathe, KS (US); Adam Rogers, Overland Park, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 139 days.

(21) Appl. No.: 17/077,487

(22) Filed: Oct. 22, 2020

(65) Prior Publication Data

US 2022/0125444 A1    Apr. 28, 2022

(51) Int. Cl.
| | | |
|---|---|---|
| *A61B 17/16* | (2006.01) | |
| *A61F 2/44* | (2006.01) | |
| *A61B 90/00* | (2016.01) | |
| *A61F 2/46* | (2006.01) | |

(52) U.S. Cl.
CPC ...... *A61B 17/1671* (2013.01); *A61B 17/1655* (2013.01); *A61B 17/1659* (2013.01); *A61F 2/44* (2013.01); *A61B 2090/3966* (2016.02); *A61F 2002/4633* (2013.01)

(58) Field of Classification Search
CPC ............... A61B 17/1655; B23G 5/00
See application file for complete search history.

(56) References Cited

U.S. PATENT DOCUMENTS

| | | |
|---|---|---|
| 6,436,101 B1 | 8/2002 | Hamada |
| 6,565,572 B2 | 5/2003 | Chappius |
| 6,582,437 B2 | 6/2003 | Dorchak et al. |
| 7,699,852 B2 | 4/2010 | Frankel et al. |
| D692,562 S | 10/2013 | Hess |
| 2008/0262555 A1 | 10/2008 | Assell et al. |
| 2012/0330360 A1 | 12/2012 | Nishida |
| 2015/0133226 A1* | 5/2015 | Osawa ............... B23B 31/11 470/198 |
| 2020/0306055 A1 | 10/2020 | Greenhalgh et al. |

FOREIGN PATENT DOCUMENTS

| | | |
|---|---|---|
| JP | H1043199 A | 2/1998 |
| WO | 2022039935 A1 | 2/2022 |

OTHER PUBLICATIONS

PCT Application No. PCT/US2021/055146, International Search Report and Written Opinion, dated Feb. 18, 2022.

* cited by examiner

*Primary Examiner* — Andrew Yang
(74) *Attorney, Agent, or Firm* — Erise IP, P.A.

(57) ABSTRACT

A system and method for providing a surgical instrument having a shaft with a proximal end, a distal end, a longitudinal axis, and a central lumen extending therethrough; and a tapered head at the distal end. The tapered head has a plurality of longitudinal channels, a plurality of threaded sections, and a plurality of lateral lumens. The plurality of longitudinal channels may form a plurality of flutes configured to cut bone, tissue, or both.

31 Claims, 5 Drawing Sheets

COMBINED BONE TAP AND RASP

BACKGROUND

1. Field

Embodiments of the invention relate to instruments for implanting spinal devices. More specifically, embodiments of the invention relate to a combined bone tap and rasp for implanting spinal implants.

2. Related Art

The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness, and/or loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, a spinal implant or spacer device is positioned behind the spinal cord or nerves and between the interspinous processes that protrude from the vertebrae in the lower back.

Examples of particularly useful interspinous process implant and fusion devices are disclosed in commonly assigned U.S. Pat. Nos. 9,861,399, 8,945,184; 9,314,276, 9,907,581, 9,757,164, and U.S. patent application Ser. No. 16/998,771, the disclosures of which are all incorporated herein by reference in their entirety.

In order to implant a spinal fusion device, the desired implant site must first be prepared. A bone rasp device may be used to initially distract the spinous processes. The bone rasp device may be used to partially remove the interspinous ligament and to partially decorticate the spinous processes for stimulating bone growth. Then, a separate bone tap device may be used to further distract the spinous processes.

An example of a graduated bone tap device is disclosed in commonly assigned U.S. Pat. No. D692,562 S, the disclosure of which is incorporated herein by reference in its entirety.

The instant invention provides an improvement over prior devices by providing a combined instrument for preparing the site for implantation, which acts as both a bone rasp and a bone tap. The device of the invention expands the space to receive the implant, removes tissue and/or bone as necessary, and also provides sizing information for the implant to the user. This improvement will advantageously reduce the number of steps in the surgical procedure, thereby making implantation safer and easier.

Additionally, the device of the present invention decorticates the bone to prepare the fusion site in a controlled and repeatable manner. The instrument design provides a maximum distance for bone cuts; thus surgeons are assured that decortication is the same for every patient. This safety measure reduces the likelihood of intraoperative spinous process fracture by placing a finite limit of the degree of decortication.

SUMMARY

Embodiments of the invention solve the above-mentioned problems by providing a surgical instrument and method for performing minimally invasive spinal surgery.

A first embodiment of the invention is directed to a surgical instrument comprising: a shaft having a proximal end, a distal end, a longitudinal axis, and a central lumen extending therethrough; and a tapered head at the distal end. The tapered head comprises a plurality of longitudinal channels, a plurality of threaded sections, and a plurality of lateral lumens. The plurality of longitudinal channels and the plurality of threaded sections are circumferentially spaced around an outer surface of the tapered head. Each lateral lumen has a first end and a second end, wherein the first end and the second end of each lateral lumen lies within one of the plurality of longitudinal channels.

A further embodiment of the invention is directed to a surgical instrument comprising: a shaft having a proximal end, a distal end, and a longitudinal axis; and a tapered head at the distal end configured to cut bone, tissue, or both. The tapered head comprises a plurality of longitudinal channels and a plurality of threaded sections circumferentially spaced around an outer surface; and a plurality of lateral lumens configured to provide sizing information. The plurality of longitudinal channels form a plurality of flutes configured to cut bone, tissue, or both.

Another embodiment of the invention is directed to a method of performing spinal surgery comprising: inserting a guidewire into a patient at a desired treatment site; inserting a combined bone rasp and tap instrument over the guidewire to distract and decorticate the spinous processes; rotating the instrument to cut bone, tissue, or both at the treatment site, such that threaded sections of the instrument are engaged with the spinous processes; viewing the plurality of lateral lumens under fluoroscopy to determine an appropriate implant size for the patient; removing the instrument from the patient; and placing a spinal implant in a patient at the desired treatment site. The combined bone rasp and tap instrument comprises a shaft having a proximal end, a distal end, a longitudinal axis, a central lumen extending therethrough, and a tapered head at the distal end. The tapered head comprises a plurality of longitudinal channels, a plurality of threaded sections, and a plurality of lateral lumens configured to provide sizing information. The plurality of longitudinal channels and the plurality of threaded sections are circumferentially spaced around an outer surface of the tapered head.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the technology can include a variety of combinations and/or integrations of the embodiments described herein.

Embodiments of the invention are directed to combined bone rasp and tap device for use in implanting a spinal implant device.

Figure 1:
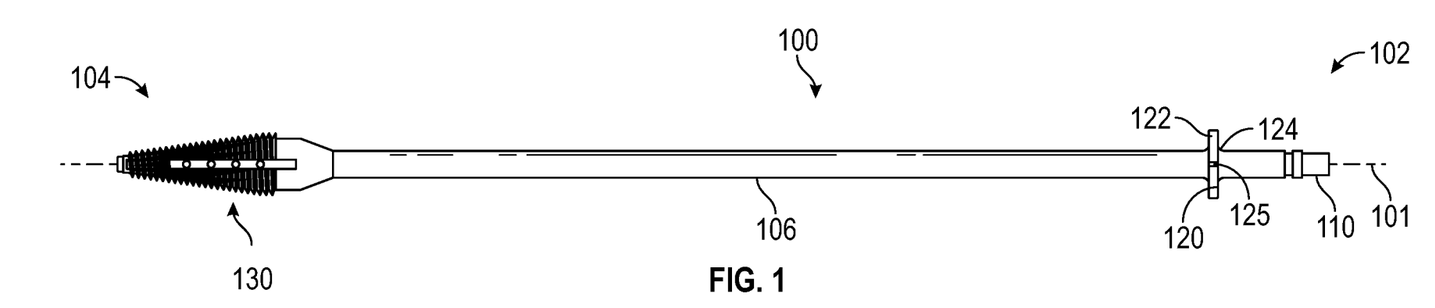
FIG. 1 is a perspective view of an embodiment of the instrument of the invention.

One embodiment of the invention is shown in FIG. 1, which illustrates a perspective view of a multi-functional instrument 100. Instrument 100 is designed to act as both a bone tap and a bone rasp. Instrument 100 includes a central longitudinal axis 101, a proximal end 102, a distal end 104, and a shaft 106 extending therebetween. In some embodiments, shaft 106 includes a central lumen 105 extending therethrough from the proximal end 102 to the distal end 104. In some embodiments, central lumen 105 has a diameter of about 2-4 mm. In some embodiments, central lumen 105 has a diameter of about 3 mm. The central lumen 105 is configured to receive a guidewire therethrough during use. In some embodiments, shaft 106 has an external diameter of about 5-15 mm along the central portion of the instrument 100. In some embodiments, shaft 106 has an external diameter of about 8 mm along the central portion of the instrument 100. As further described below, instrument 100 may also include a driver head 110 at the proximal end 102, a circumferential extension 120 near the proximal end 102, and a tapered head 130 at the distal end 104.

Figure 2:
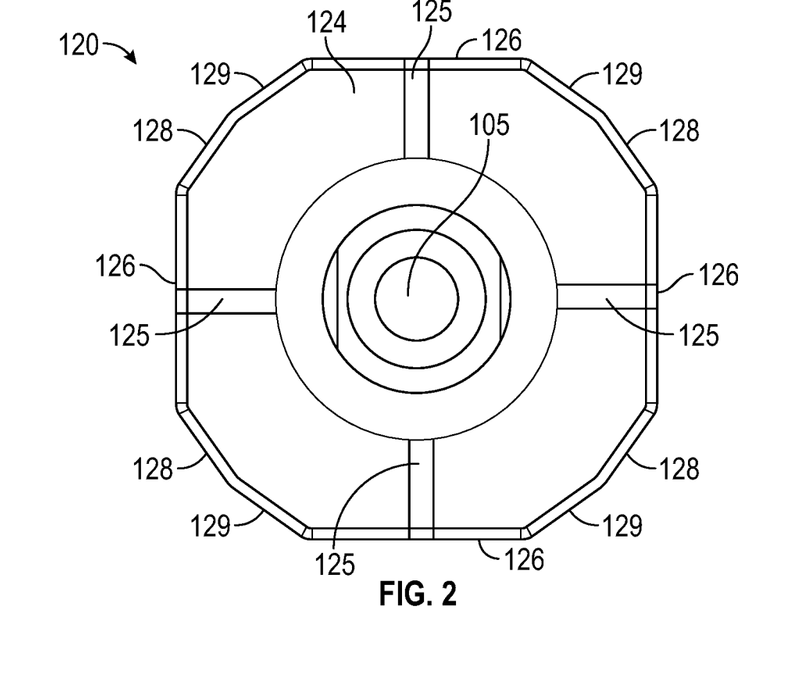
FIG. 2 is an end view of the proximal end of an embodiment of the instrument of the invention.

Extension 120 may be configured to act as a stop when the instrument 100 is received in a delivery sleeve or dilator (not shown). In one embodiment, circumferential extension 120 may be shaped as a flat plate having a planar distal side 122 and a planar proximal side 124. When viewed from the proximal end, as shown in FIG. 2, extension 120 may be shaped such that the planar surface has four substantially flat sides 126. In some embodiments, each side 126 may be connected by two additional flat segments 128, 129, such that the whole circumferential shape has twelve sides. In some embodiments, the sides 126 may be connected by substantially rounded segments. In some embodiments, each side 126 may be connected by a single flat segment, such that the whole shape has eight sides, and may form an octagon. In other embodiments, the extension 120 may be shaped such that the planar surface is approximately circular. Extension 120 may have an outer diameter of about 15-30 mm. In some embodiments, the length of sides 126 may be about 8-20 mm. In some embodiments, the sides 126 are all the same length. In other embodiments, the length of each of the sides 126 may vary. In some embodiments, the segments 128 and 129 are all the same length. In other embodiments, the length of each of the segments 128 and 129 may vary.

Figure 3:
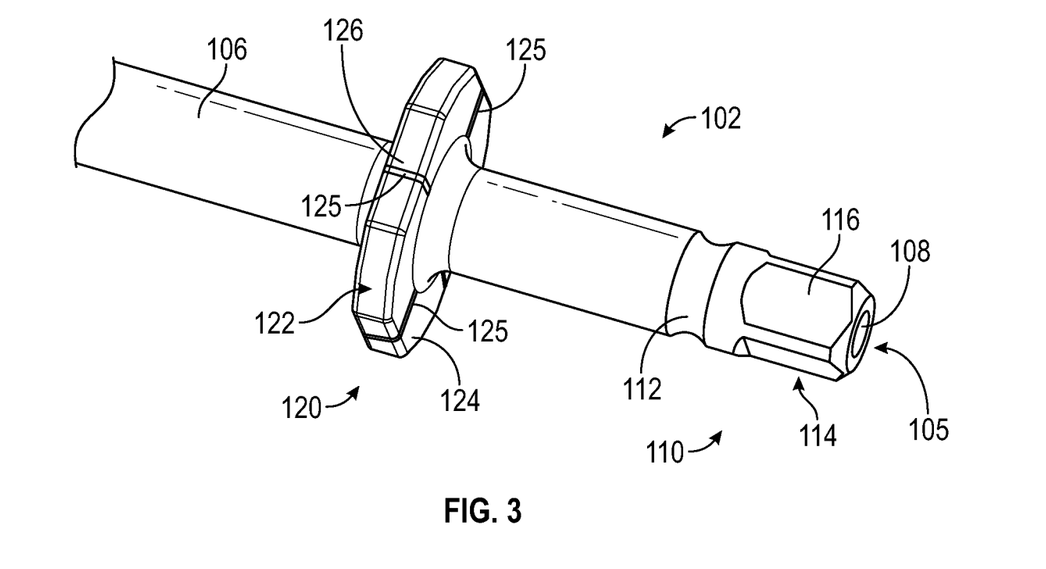
FIG. 3 is a perspective view of the proximal end of an embodiment of the instrument of the invention.

Planar proximal side 124, planar distal side 122, and/or sides 126 may include markings 125, such as laser-etched markings, that may be viewable by a user during delivery when the extension 120 remains outside the patient. Markings 125 are circumferentially aligned with the location of the ends of the lateral lumens 160, 170 for determining the implant size, which will be further described below with respect to FIG. 7. A user can thus properly align the lateral lumen openings to the field of the c-arm prior to taking an image to limit the number of images that need to be taken and reduce fluoro-exposure, As shown in FIG. 3, in some embodiments, proximal end 102 includes a driver head 110 located proximally of the extension 120. An annular channel 112 is located at the proximal side of the driver head 110. In some embodiments, driver head includes an approximately square portion 114 having four flat sides 116 for cooperating with a driver instrument (not shown) during use. In some embodiments, driver head 110 is a quick-connect attachment, such as a ¼ inch square quick connect head, that can be connected to any known driver instrument. In some embodiments, the driver head 110 may comprise any known quick-connect attachment mechanism. In some embodiments, the proximal end of driver head 110 has an opening 108 for accessing central lumen 105.

Figure 4:
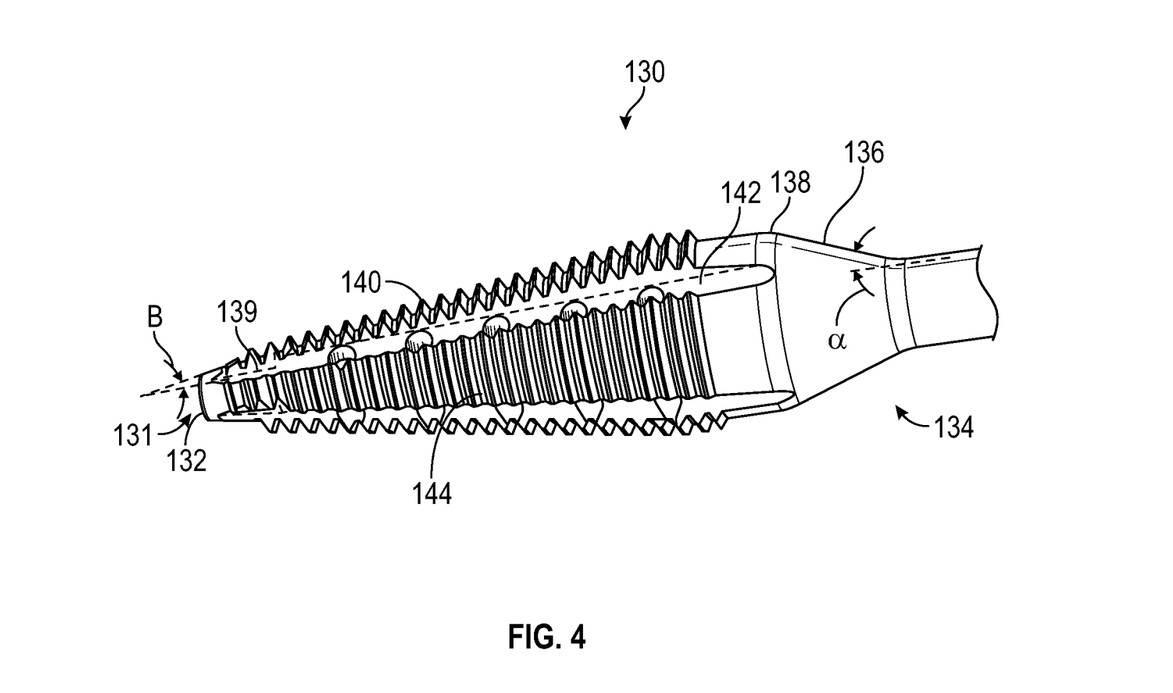
FIG. 4 is a perspective view of the distal end of an embodiment of the instrument of the invention.
Figure 5:
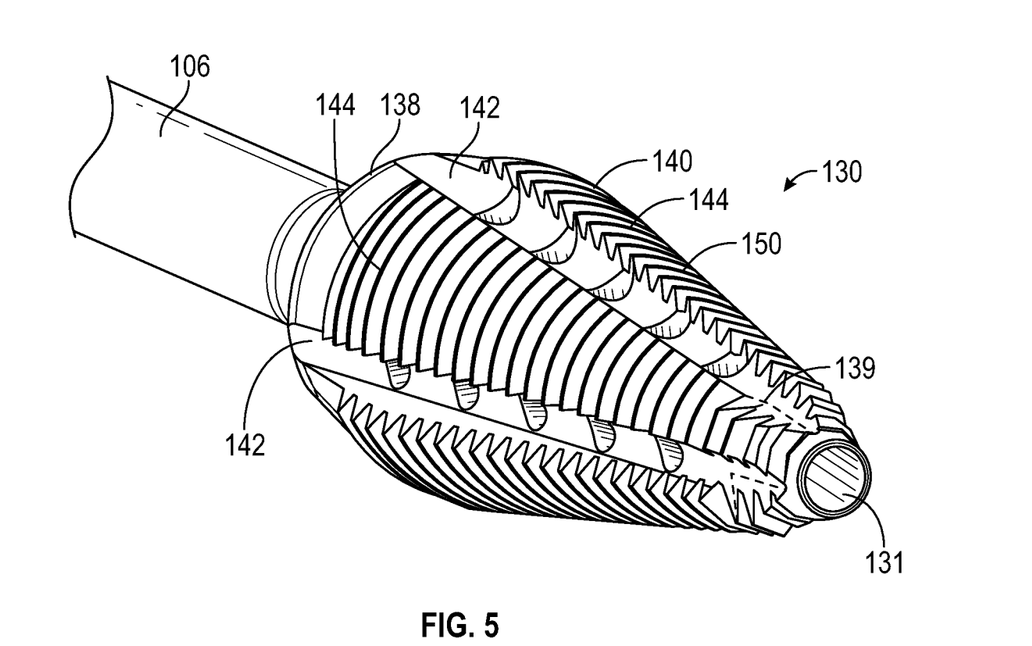
FIG. 5 is a perspective view of the distal end of an embodiment of the instrument of the invention.

As shown in FIGS. 4 and 5, distal end 104 includes a tapered head 130 having a substantially flat distal tip 132 and a proximal section 134. In some embodiments, the distal tip may alternatively be sharp, pointed, or substantially rounded. The distal end of tapered head 130 has a central distal opening 131 for accessing central lumen 105.

Proximal section 134 has a sloped wall 136 extending circumferentially outwardly from the central shaft 106 at an angle α from the central longitudinal axis 101 to form an enlarged diameter section. In some embodiments, side wall 136 of proximal section 134 of tapered head 130 may extend at an angle α of about 0-90° from the longitudinal axis 101. In some embodiments, side wall 136 of proximal section 134 of tapered head 130 may extend at an angle α of about 10-50° from the longitudinal axis 101. In some embodiments, side wall 136 is sloped at an angle of about 20° from the longitudinal axis 101. Proximal section 134 has a diameter of about 16-20 mm at its largest dimension at area 138. Area 138 of proximal section 134 intersects with wall 140, which forms the base of the conical shape of tapered head 130. In some embodiments, side wall 140 of tapered head 130 is sloped at an angle B of about 3-25° from the longitudinal axis 101. In some embodiments, side wall 140 is sloped at an angle of about 8° from the longitudinal axis 101. In some embodiments, angle α is greater than angle B. In some embodiments, angle α is less than angle B. In some embodiments, angle α is equal to angle B.

With respect to FIG. 5, outer surface of side wall 140 of tapered head 130 may include a plurality of longitudinal channels 142 and a plurality of threaded sections 144. In some embodiments, tapered head 130 includes four longitudinal channels 142 evenly spaced between four threaded sections 144, such that the longitudinal channels are spaced 90° apart circumferentially. In other embodiments, tapered head 130 may include two longitudinal channels and two threaded sections, or alternatively may include three longitudinal channels and three threaded sections. In some embodiments, the longitudinal channels 142 are straight, extending parallel with respect to the longitudinal axis 101. In some embodiments, the longitudinal channels 142 may include a slight turn at the distal end creating a sharpened distal cutting flute 139. Cutting flute 139 acts as a self-drilling feature to reduce the amount of insertion force needed to start insertion of the instrument into the interspinous space. In some embodiments, the longitudinal channels 142 may be curved such that they rotate around the outer surface. In some embodiments, longitudinal channels 142 and threaded sections 144 may be unevenly spaced circumferentially around the tapered head 130. As can be seen in the cross-sectional end view of FIG. 6, the longitudinal channels 142 and threaded sections 144 create a substantially circular cross-sectional shape 146 having a plurality of cut-outs 148 formed by the longitudinal channels 142. In some embodiments, one or both of the longitudinal edges of the cut-outs 148 can be sharpened to create flutes, which facilitate cutting into the bone/tissue as the instrument 100 is inserted. In some embodiments, the longitudinal channels 142 are asymmetrical such that a cutting flute is formed on only one longitudinal edge thereof.

Threaded sections 144 may extend along the entire length of the tapered head 130 or along any portion thereof. In some embodiments, all threaded sections 144 do not extend over the same length. Threaded sections 144 may be continuous or dis-continuous. Threaded sections 144 are shaped such that they can cut bone and/or tissue. Threaded sections 144 may include threads 150 are sharp such that they include a cutting distal edge. In some embodiments, the threaded sections 144 include helical threads. In some embodiments, the threaded sections 144 include box threads. In some embodiments, each threaded section 144 may include multiple helical threads.

In some embodiments, the pitch of threads 150 may be from about 1.5 mm to about 2.0 mm. In some embodiments, the pitch of threads 150 may be about 1.75 mm. In some embodiments, the pitch of threads 150 may be matched to the pitch of the threads of the implant that is to be used. In some embodiments, the depth of threads 150 may be from about 2.0 mm to about 0.5 mm. In some embodiments, the depth of threads 150 may be about 1.00 mm. In some embodiments, threads 150 may have a thread angle of about 10° to about 75°. In some embodiments, threads 150 may have a thread angle of about 60°. In some embodiments, each threaded section may have multiple portions having different dimensional parameters. In some embodiments, some or all of the threaded sections 144 may have threads 150 with different dimensional parameters, such as pitch, depth, and angle.

Figure 6:
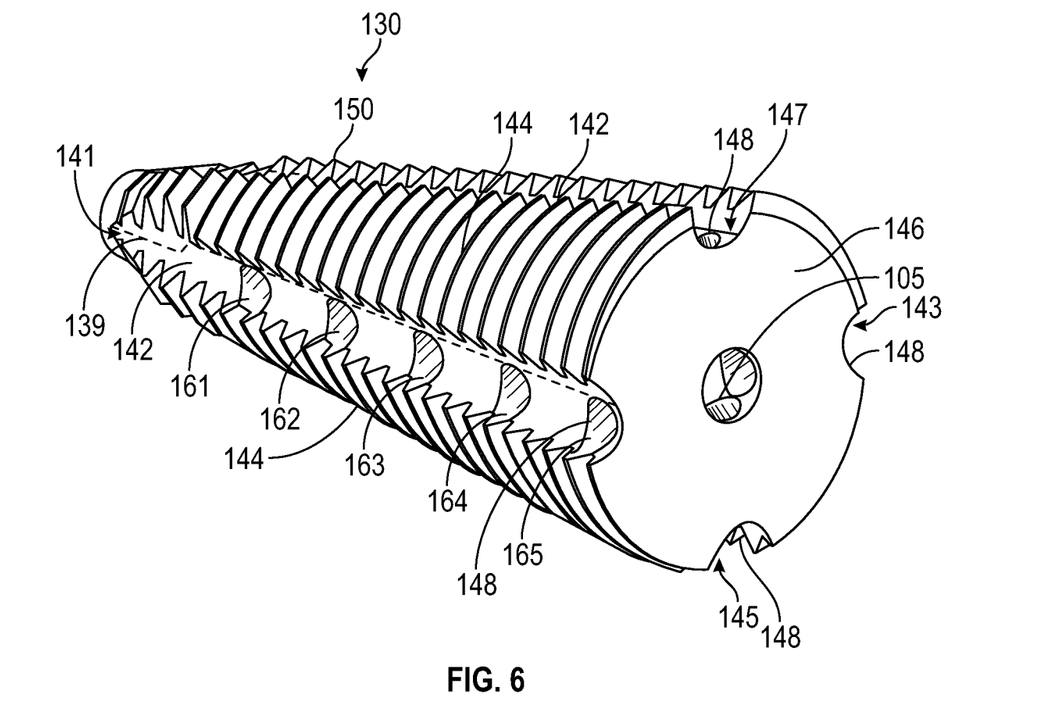
FIG. 6 is a cross-sectional view of the distal end of an embodiment of the instrument of the invention.

As seen in FIG. 6, tapered head 130 may include two sets of lateral lumens 160, 170. In some embodiments, first set of lateral lumens 160 includes lumens 161, 162, 163, 164, and 165. In some embodiments, second set of lateral lumens 170 includes lumens 171, 172, 173, 174, and 175. In one embodiment, a first end of the set of lateral lumens 160 lies within a first channel 141 and a second end of the set of lateral lumens 160 lies within a second channel 143, which is spaced circumferentially 180 degrees from the first channel 141. Similarly, in this embodiment, a first end of the set of lateral lumens 170 lies within a third channel 145 and a second end of the set of lateral lumens 170 lies within a fourth channel 147 that is spaced circumferentially 180 degrees from the third channel 145. Arranging the lateral lumens 160, 170 to have the ends located in the longitudinal channels 142 improves the ease of manufacturing and reduces burr creation during manufacturing. In one embodiment, first channel 141, second channel 143, third channel 145, and fourth channel 147 are spaced 90 degrees apart from each other, as seen in FIG. 6. In some embodiments, first channel 141, second channel 143, third channel 145, and fourth channel 147 are spaced asymmetrically around the central longitudinal axis. In some embodiments, the lateral lumens 160, 170 extend perpendicular to the longitudinal axis. In other embodiments, the lateral lumens 160, 170 may extend at an angle relative to the longitudinal axis such that they each form a V-shape. In some embodiments, the ends of the lateral lumens 160, 170 are located within the threaded sections 144.

Figure 7:
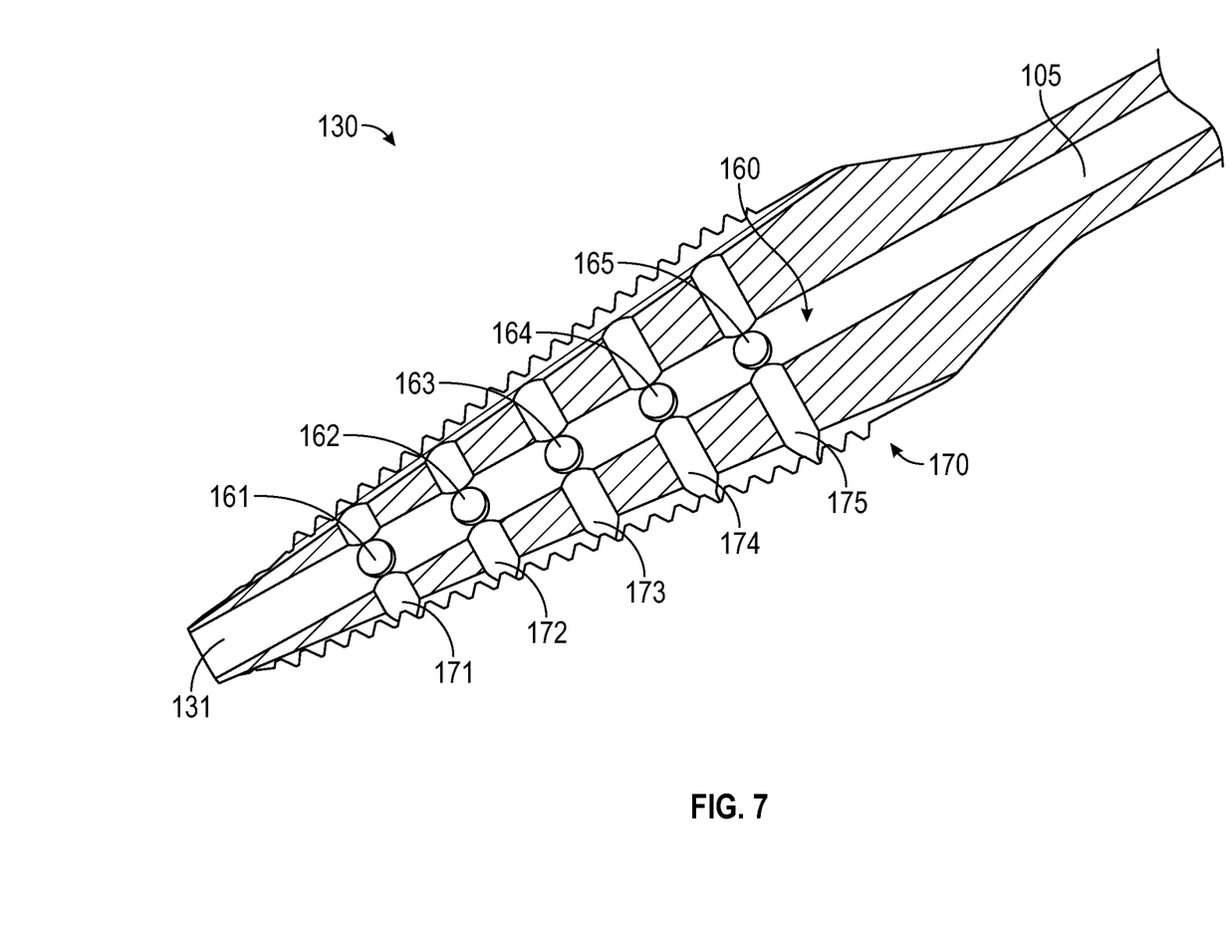
FIG. 7 is a cross-sectional view of the distal end of an embodiment of the instrument of the invention.

As shown in FIG. 7, in some embodiments, each of the lumens 161, 162, 163, 164, 165 and 171, 172, 173, 174, 175 are spaced along the tapered head 130 so as to denote the size of the implant that is to be used. Specifically, the outer ends of lumens 161 and 171 may be located such that they correspond to an 8 mm minor diameter of the tapered head 130 and thereby correspond to an implant sized 8 mm. The outer ends of lumens 162 and 172 may be located such that they correspond to a 10 mm minor diameter of the tapered head 130 and thereby correspond to an implant sized 10 mm. The outer ends of lumens 163 and 173 may be located such that they correspond to a 12 mm minor diameter of the tapered head 130 and thereby correspond to an implant sized 12 mm. The outer ends of lumens 164 and 174 may be located such that they correspond to a 14 mm minor diameter of the tapered head 130 and thereby correspond to an implant sized 14 mm. The outer ends of lumens 165 and 175 may be located such that they correspond to a 16 mm minor diameter of the tapered head 130 and thereby correspond to an implant sized 16 mm. These lumens may be seen under fluoroscopy such that a user may choose the appropriate size implant: 8 mm, 10 mm, 12 mm, 14 mm or 16 mm. In other embodiments, other dimensions may correspond to differently placed lumen spacing. In other embodiments, instead of lateral lumens, a fluorescent material or other visible markings may be placed at particular spaced locations along the tapered head 130 to demarcate the implant sizes.

In some embodiments, all or part of the instrument 100 may be composed of titanium or a titanium alloy. In other embodiments, all or part of the instrument 100 may be composed of stainless steel. In some embodiments, all or part of the instrument 100 may be composed of a polymer or a bioabsorbable material.

Figure 8:
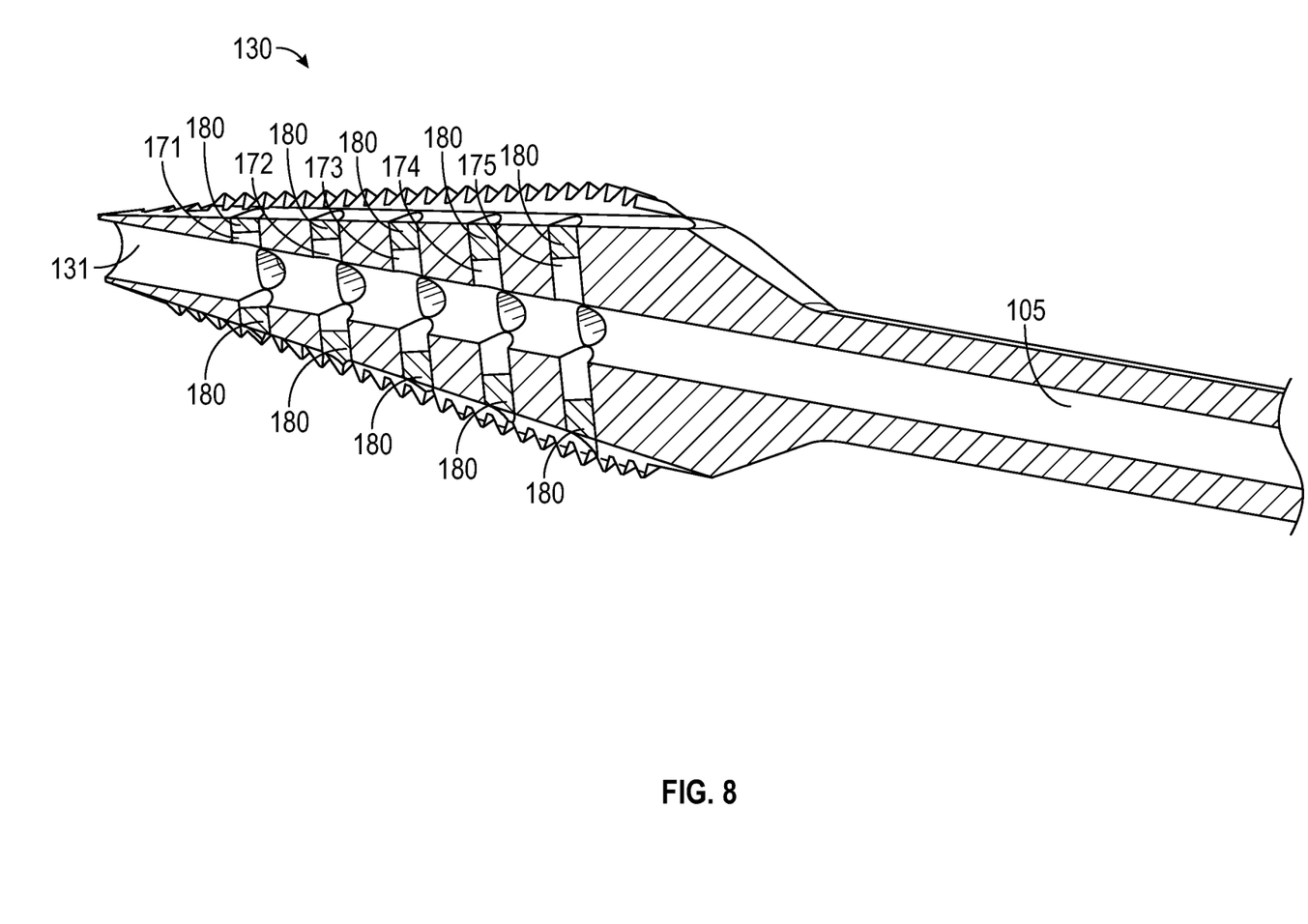
FIG. 8 is a cross-sectional view of the distal end of an embodiment of the instrument of the invention.

In embodiments in which the material of the tapered head 130 is composed of a material that would not be viewable on an imaging device, radiopaque or radiolucent pegs 180 may be inserted into the lateral lumens 160, 170 such that the lumen locations may be viewable for sizing. As seen in FIG. 8, radiopaque or radiolucent pegs 180 may extend only partially through lateral lumens 160, 170 such that they will not obstruct the central lumen 105. In some embodiments, pegs 180 may be placed in some or all of the lateral lumens 160, 170.

In some embodiments, the instrument may be manufactured by an additive manufacturing process. In some embodiments, the instrument may be manufactured by machining or molding. In some embodiments, all or part of the instrument may include a coating on at least one surface thereof. In some embodiments, at least one outer surface of the instrument may be coated with a friction-reducing coating, such as chrome In one embodiment, the instrument 100 may be used to prepare the site for a spinal fusion implant. For a spinal implant procedure, a patient may be placed in a prone position on a frame to decrease the lordosis of the spine and avoid compression of the abdomen. The surgeon may tilt the pelvis by inclining the surgical table at the level of the pelvis, allowing for natural distraction of the spinous processes. Using a lateral minimally invasive surgical (MIS) approach, an incision may be made and a guide wire may be introduced into the patient's body, which may be done using an aiming device under fluoroscopy. The guidewire is then advanced between the spinous processes and pierces the interspinous ligament. Once the guidewire is advanced as desired, which may be approximately 2 cm across the midline of the spine, the aiming device may be removed with the guidewire remaining in place. A guidewire extension may be placed on the proximal end of the guidewire to help maintain guidewire placement during the procedure. A series of blunt dilators may then be placed over the guidewire to create a pathway to the spinous processes, which are then removed with the guidewire remaining in place.

The instrument 100 may then be inserted over the guidewire. Instrument 100 may be used to distract the spinous processes, remove the interspinous ligament, and partially decorticate the spinous processes for stimulating bone growth. Instrument 100 may be rotated clockwise to gradually decorticate and/or to distract the spinous processes. The instrument 100 may be threaded into the interspinous process space such that the threads 150 are engaged with the spinous processes and tap a path for the implant to be inserted along. Once adequate distraction is obtained, the degree of distraction can be determined by viewing under fluoroscopy which lumen of the set of lateral lumens 160, 170 is positioned between the spinous processes. This degree of distraction thereby determines the appropriate implant size, which may be a 8 mm, 10 mm, 12 mm, 14 mm, or 16 mm implant. Instrument 100 replaces the use of a multiple separate bone rasps and a separate bone tap, which would be inserted in multiple steps. In cases where the spinous processes in the patient are initially touching, the design of the instrument 100 is especially useful in that the cutting flutes and gradual taper of the tapered head 130 can more easily fit into the desired space. The ease and safety of the procedure is thus improved by use of combined rasp/tap instrument 100. The instrument 100 and the guidewire can then be removed and the spinal implant can be placed.

Features described above as well as those claimed below may be combined in various ways without departing from the scope hereof. The following examples illustrate some possible, non-limiting combinations:

(A1) A surgical instrument comprising: a shaft having a proximal end, a distal end, a longitudinal axis, and a central lumen extending therethrough; and a tapered head at the distal end. The tapered head comprises a plurality of longitudinal channels, a plurality of threaded sections, and a plurality of lateral lumens. The plurality of longitudinal channels and the plurality of threaded sections are circumferentially spaced around an outer surface of the tapered head. Each lateral lumen has a first end and a second end, wherein the first end and the second end of each lateral lumen lies within one of the plurality of longitudinal channels.

(A2) For the surgical instrument denoted as (A1), the plurality of threaded sections comprise threads having a shape configured to cut bone, tissue, or both.

(A3) For the surgical instrument denoted as (A1) or (A2), the plurality of threaded sections comprise threads having a thread angle of about 60 degrees.

(A4) For the surgical instrument denoted as any of (A1) through (A3), further comprising a plurality of radiopaque pegs or radiolucent pegs received within at least one of the plurality of lateral lumens.

(A5) For the surgical instrument denoted as any of (A1) through (A4), the tapered head comprises: a first sloped side wall extending from the distal end at a first angle relative to the longitudinal axis, and a second sloped side wall intersecting with the first sloped side wall to form an enlarged diameter proximal section. The second sloped side wall extends circumferentially outwardly from the central shaft at a second angle relative to the longitudinal axis.

(A6) For the surgical instrument denoted as any of (A1) through (A5), each of the plurality of lateral lumens extend perpendicular to the longitudinal axis.

(A7) For the surgical instrument denoted as any of (A1) through (A6), the plurality of lateral lumens comprise a first set of lateral lumens and a second set of lateral lumens arranged at approximately 90 degrees relative to each other.

(A8) For the surgical instrument denoted as any of (A1) through (A7), further comprising: a circumferential extension near the proximal end.

(B1) A surgical instrument comprising: a shaft having a proximal end, a distal end, and a longitudinal axis; and a tapered head at the distal end configured to cut bone, tissue, or both. The tapered head comprises a plurality of longitudinal channels and a plurality of threaded sections circumferentially spaced around an outer surface; and a plurality of lateral lumens configured to provide sizing information. The plurality of longitudinal channels form a plurality of flutes configured to cut bone, tissue, or both.

(B2) For the surgical instrument denoted as (B1), further comprising: a circumferential extension near the proximal end.

(B3) For the surgical instrument denoted as (B1) or (B2), each lateral lumen has a first end and a second end, and wherein the first end and the second end of each lateral lumen lies within one of the plurality of longitudinal channels.

(B4) For the surgical instrument denoted as any of (B1) through (B3), the plurality of threaded sections comprise threads having a shape configured to cut bone, tissue, or both.

(B5) For the surgical instrument denoted as any of (B1) through (B4), the plurality of threaded sections comprise threads having a thread angle of about 50-75 degrees.

(B6) For the surgical instrument denoted as any of (B1) through (B5), further comprising a plurality of radiopaque pegs or radiolucent pegs received within at least one of the plurality of lateral lumens.

(B7) For the surgical instrument denoted as any of (B1) through (B6), each of the plurality of lateral lumens extends perpendicular to the longitudinal axis.

(B8) For the surgical instrument denoted as any of (B1) through (B7), further comprising: a central lumen extending through the shaft.

(C1) A method of performing spinal surgery comprising: inserting a guidewire into a patient at a desired treatment site; inserting a combined bone rasp and tap instrument over the guidewire to distract and decorticate the spinous processes; rotating the instrument to cut bone, tissue, or both at the treatment site, such that threaded sections of the instrument are engaged with the spinous processes; viewing the plurality of lateral lumens under fluoroscopy to determine an appropriate implant size for the patient; removing the instrument from the patient; and placing a spinal implant in a patient at the desired treatment site. The combined bone rasp and tap instrument comprises a shaft having a proximal end, a distal end, a longitudinal axis, a central lumen extending therethrough, and a tapered head at the distal end. The tapered head comprises a plurality of longitudinal channels, a plurality of threaded sections, and a plurality of lateral lumens configured to provide sizing information. The plurality of longitudinal channels and the plurality of threaded sections are circumferentially spaced around an outer surface of the tapered head.

(C2) For the method denoted as (C1), the instrument further comprises a circumferential extension near the proximal end. The circumferential extension acts as a stop to prevent the instrument from being inserted too far into a patient's body.

(C3) For the method denoted as (C1) or (C2), the first end and the second end of each lateral lumen lies within one of the plurality of longitudinal channels.

(C4) For the method denoted as any of (C1) through (C3), further comprising placing a plurality of radiopaque pegs or radiolucent pegs within at least one of the plurality of lateral lumens before use.

(C5) For the method denoted as any of (C1) through (C4), the plurality of threaded sections comprise threads having a shape configured to cut bone, tissue, or both.

(C6) For the method denoted as any of (C1) through (C5), the tapered head further comprises: a first sloped side wall extending from the distal end at a first angle relative to the longitudinal axis; and a second sloped side wall intersecting with the first sloped side wall to form an enlarged diameter proximal section. The second sloped side wall extends circumferentially outwardly from the central shaft at a second angle relative to the longitudinal axis.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A surgical instrument comprising:
   a shaft having a proximal end, a distal end, a longitudinal axis, and a central lumen extending therethrough; and
   a tapered head at the distal end, said tapered head comprising:
      a plurality of longitudinal channels and a plurality of threaded sections, the plurality of longitudinal channels and the plurality of threaded sections being circumferentially spaced around an outer surface; and
      a plurality of lateral lumens, each lateral lumen having a first end and a second end,
      wherein the first end and the second end of each lateral lumen lies within one of the plurality of longitudinal channels, and
      wherein at least one of the plurality of lateral lumens receives radiopaque or radiolucent material.

2. The surgical instrument of claim 1,
   wherein the plurality of threaded sections comprise threads having a shape configured to cut bone, tissue, or both.

3. The surgical instrument of claim 1,
   wherein the plurality of threaded sections comprise threads having a thread angle of about 50-75 degrees.

4. The surgical instrument of claim 1,
   wherein the tapered head comprises:
      a first sloped side wall extending from the distal end at a first angle relative to the longitudinal axis; and
      a second sloped side wall intersecting with the first sloped side wall to form an enlarged diameter proximal section,
         said second sloped side wall extending circumferentially outwardly from the shaft at a second angle relative to the longitudinal axis.

5. The surgical instrument of claim 1,
   wherein each of the plurality of lateral lumens extends perpendicular to the longitudinal axis.

6. The surgical instrument of claim 1,
   wherein the plurality of lateral lumens comprise:
      a first set of lateral lumens and a second set of lateral lumens arranged at approximately 90 degrees relative to each other.

7. A surgical instrument comprising:
   a shaft having a proximal end, a distal end, and a longitudinal axis;
   a tapered head at the distal end configured to cut bone, tissue, or both, said tapered head comprising:
      a plurality of longitudinal channels and a plurality of threaded sections circumferentially spaced around an outer surface,
      said plurality of longitudinal channels forming a plurality of sharpened flutes configured to cut bone, tissue, or both; and
      a plurality of lateral lumens configured to provide sizing information,
         wherein at least one of the plurality of lateral lumens receives radiopaque or radiolucent material.

8. The surgical instrument of claim 7, further comprising:
a circumferential extension near the proximal end.
9. The surgical instrument of claim 7,
wherein each lateral lumen has a first end and a second end, and wherein the first end and the second end of each lateral lumen lies within one of the plurality of longitudinal channels.
10. The surgical instrument of claim 7,
wherein the plurality of threaded sections comprise threads having a shape configured to cut bone, tissue, or both.
11. The surgical instrument of claim 7,
wherein the plurality of threaded sections comprise threads having a thread angle of about 50-75 degrees.
12. The surgical instrument of claim 7,
wherein each of the plurality of lateral lumens extends perpendicular to the longitudinal axis.
13. A method of performing spinal surgery comprising:
inserting a guidewire into a patient at a desired treatment site;
inserting a combined bone rasp and tap instrument over the guidewire to distract and decorticate the spinous processes, said instrument comprising:
  a shaft having a proximal end, a distal end, a longitudinal axis, and a central lumen extending therethrough; and
  a tapered head at the distal end, said tapered head comprising:
    a plurality of longitudinal channels and a plurality of threaded sections, the plurality of longitudinal channels and the plurality of threaded sections being circumferentially spaced around an outer surface; and
    a plurality of lateral lumens configured to provide sizing information;
rotating the instrument to cut bone, tissue, or both at the treatment site, such that at least one of the plurality of threaded sections of the instrument is engaged with the spinous processes;
viewing the plurality of lateral lumens under fluoroscopy to determine an appropriate implant size for the patient;
removing the instrument from the patient; and
placing a spinal implant in the patient at the desired treatment site.
14. The method of claim 13,
wherein the instrument further comprises:
  a circumferential extension near the proximal end, wherein said circumferential extension acts as a stop to prevent the instrument from being inserted too far into a patient's body.
15. The method of claim 13,
wherein each lateral lumen has a first end and a second end, wherein the first end and the second end of each lateral lumen lies within one of the plurality of longitudinal channels.
16. The method of claim 13, further comprising:
placing a plurality of radiopaque pegs or radiolucent pegs within at least one of the plurality of lateral lumens before use.
17. The method of claim 13,
wherein the plurality of threaded sections comprise threads having a shape configured to cut bone, tissue, or both.
18. The method of claim 13,
wherein the tapered head further comprises:
  a first sloped side wall extending from the distal end at a first angle relative to the longitudinal axis; and
  a second sloped side wall intersecting with the first sloped side wall to form an enlarged diameter proximal section,
    said second sloped side wall extending circumferentially outwardly from the shaft at a second angle relative to the longitudinal axis.
19. A surgical instrument comprising:
a shaft having a proximal end, a distal end, a longitudinal axis, and a central lumen extending therethrough; and
a tapered head at the distal end, said tapered head comprising:
  a first sloped side wall extending from the distal end at a first angle relative to the longitudinal axis;
  a second sloped side wall intersecting with the first sloped side wall to form an enlarged diameter proximal section, the second sloped side wall extending circumferentially outwardly from the shaft at a second angle relative to the longitudinal axis;
  a plurality of longitudinal channels and a plurality of threaded sections, the plurality of longitudinal channels and the plurality of threaded sections being circumferentially spaced around an outer surface of the first sloped side wall; and
  a plurality of lateral lumens, each lateral lumen having a first end and a second end,
wherein the first end and the second end of each lateral lumen lies within one of the plurality of longitudinal channels.
20. The surgical instrument of claim 19,
wherein at least a portion of the tapered head is sized and configured to cut bone, tissue, or both.
21. The surgical instrument of claim 19,
wherein the first sloped side wall extends from the distal end at an angle of 8 degrees relative to the longitudinal axis.
22. The surgical instrument of claim 21,
wherein the second sloped side wall extends circumferentially outwardly from the shaft at an angle of 10-50 degrees from the longitudinal axis.
23. The surgical instrument of claim 19, further comprising:
a circumferential extension near the proximal end.
24. The surgical instrument of claim 23,
wherein the circumferential extension comprises a plurality of flat sides, the plurality of flat sides forming the shape of an octagon.
25. The surgical instrument of claim 24,
wherein at least one flat side of the plurality of flat sides comprises markings aligned with the location of the first end or the second end of at least one of the plurality of lateral lumens.
26. A surgical instrument comprising:
a shaft having a proximal end, a distal end, a longitudinal axis, and a central lumen extending therethrough; and
a tapered head at the distal end, said tapered head comprising:
  a plurality of longitudinal channels and a plurality of threaded sections, the plurality of longitudinal channels and the plurality of threaded sections being circumferentially spaced around an outer surface; and
  a plurality of lateral lumens comprising a first set of lateral lumens and a second set of lateral lumens arranged at approximately 90 degrees relative to each other, each lateral lumen having a first end and a second end, wherein the first end and the second end of each lateral lumen lies within one of the plurality of longitudinal channels.

27. The surgical instrument of claim 26,
wherein the tapered head comprises:
  a first sloped side wall extending from the distal end at a first angle relative to the longitudinal axis; and
  a second sloped side wall intersecting with the first sloped side wall to form an enlarged diameter proximal section,
    said second sloped side wall extending circumferentially outwardly from the shaft at a second angle relative to the longitudinal axis.

28. The surgical instrument of claim 27,
wherein the first sloped side wall extends from the distal end at an angle of 8 degrees relative to the longitudinal axis.

29. The surgical instrument of claim 28,
wherein the second sloped side wall extends circumferentially outwardly from the shaft at an angle of 10-50 degrees from the longitudinal axis.

30. The surgical instrument of claim 26,
further comprising a radiopaque or radiolucent material received within at least one of the plurality of lateral lumens.

31. The surgical instrument of claim 26,
wherein at least a portion of the tapered head is sized and configured to cut bone, tissue, or both.

* * * * *